(12) United States Patent
D'arrigo Guiseppe et al.

(10) Patent No.: US 7,063,798 B2
(45) Date of Patent: Jun. 20, 2006

(54) METHOD FOR REALIZING MICROCHANNELS IN AN INTEGRATED STRUCTURE

(75) Inventors: Alessio M. D'arrigo Guiseppe, Sant' Agata li Battiati (IT); Rosario C. Spinella, Catania (IT); Guiseppe Arena, Catania (IT); Simona Lorenti, Catania (IT)

(73) Assignee: STMicroelectronics S.r.l. (IT)

( * ) Notice: Subject to any disclaimer, the term of this patent is extended or adjusted under 35 U.S.C. 154(b) by 182 days.

(21) Appl. No.: 10/726,264

(22) Filed: Dec. 2, 2003

(65) Prior Publication Data

US 2004/0217447 A1    Nov. 4, 2004

(30) Foreign Application Priority Data

Dec. 4, 2002    (EP)    .................... 02425746

(51) Int. Cl.
*H01L 21/00*    (2006.01)
*B44C 1/22*    (2006.01)

(52) U.S. Cl. .............. 216/67; 216/2; 216/17; 216/18; 216/57; 216/83; 438/689; 438/733; 438/734

(58) Field of Classification Search ............ 216/2, 216/17, 18, 67, 57, 83; 438/689, 733, 734
See application file for complete search history.

(56) References Cited

U.S. PATENT DOCUMENTS

| 4,685,198 | A | | 8/1987 | Kawakita |
| 4,993,143 | A | | 2/1991 | Sidner |
| 5,429,734 | A | | 7/1995 | Gajar |
| 6,153,488 | A | * | 11/2000 | Yoshino ................... 438/345 |
| 6,376,291 | B1 | | 4/2002 | Barlocchi |
| 6,406,982 | B1 | * | 6/2002 | Urakami et al. ........... 438/492 |
| 6,426,254 | B1 | * | 7/2002 | Kudelka et al. ........... 438/246 |
| 6,582,987 | B1 | * | 6/2003 | Jun et al. ................. 438/49 |
| 2001/0049200 | A1 | * | 12/2001 | Erratico et al. ........... 438/701 |
| 2002/0086456 | A1 | * | 7/2002 | Cunningham et al. ....... 438/57 |
| 2002/0132421 | A1 | * | 9/2002 | Schrems ................... 438/241 |

FOREIGN PATENT DOCUMENTS

| EP | 1 043 770 | 10/2000 |
| EP | 1 067 599 | 1/2001 |
| EP | 1 073 112 | 1/2001 |
| WO | WO 01/61750 | 8/2001 |

OTHER PUBLICATIONS

European Search Report, 02425746.1, dated Jul. 15, 2003.

* cited by examiner

*Primary Examiner*—Shamim Ahmed
(74) *Attorney, Agent, or Firm*—Jenkens & Gilchrist, PC

(57) ABSTRACT

A process is presented for realizing buried microchannels (10) in an integrated structure (1) comprising a monocrystalline silicon substrate (2). The process forms in the substrate (2) at least one trench (4). A microchannel (10) is obtained starting from a small surface port of the trench (4) by anisotropic etching of the trench. The microchannel (10) is then completely buried in the substrate (2) by growing a microcrystalline structure to enclose the small surface port.

35 Claims, 5 Drawing Sheets

METHOD FOR REALIZING MICROCHANNELS IN AN INTEGRATED STRUCTURE

PRIORITY CLAIM

The present application claims priority from European Application for Patent No. 02425746.1 filed Dec. 4, 2002, the disclosure of which is hereby incorporated by reference.

BACKGROUND OF THE INVENTION

1. Technical Field of the Invention

The present invention relates to a process for realizing microchannels in an integrated structure. More specifically, the invention relates to a process for realizing microchannels buried in an integrated structure comprising a monocrystalline silicon substrate.

2. Description of Related Art

Typical procedures for analyzing biological materials, such as nucleic acid, involve a variety of operations starting from raw material. These operations may include various degrees of cell purification, lysis, amplification or purification, and analysis of the resulting amplification or purification product.

As an example, in DNA-based blood tests the samples are often purified by filtration, centrifugation or by electrophoresis so as to eliminate all the non-nucleated cells. Then, the remaining white blood cells are lysed using chemical, thermal or biochemical means in order to liberate the DNA to be analyzed. Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

The procedures are similar if RNA is to be analyzed, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof. In an analysis by hybridization, for example, the amplified DNA is passed over a plurality of detectors made up of individual oligonucleotide detector "probes" that are anchored, for example, on electrodes. If the amplified DNA strands are complementary to the probes, stable bonds will be formed between them and the hybridized detectors can be read by observation by a wide variety of means, including optical, electrical, magnetic, mechanical or thermal means.

Other biological molecules are analyzed in a similar way, but typically molecule purification is substituted for amplification and detection methods vary according to the molecule being detected. For example, a common diagnostic involves the detection of a specific protein by binding to its antibody or by a specific enzymatic reaction. Lipids, carbohydrates, drugs and small molecules from biological fluids are processed in similar ways. However, we have simplified the discussion herein by focusing on nucleic acid analysis, in particular DNA amplification, as an example of a biological molecule that can be analyzed using the devices of the invention.

The steps of nucleic acid analysis described above are currently performed using different devices, each of which presides over one aspect of the process. The use of separate devices increases cost and decreases the efficiency of sample processing because transfer time between devices is required, larger samples are required to accommodate sample loss and instrument size, and because qualified operators are required to avoid contamination problems. For these reasons an integrated microreactor would be preferred.

For performing treatment of fluids, integrated microreactors of semiconductor material are already known. Microchannel arrays are widely used in different systems such as medical systems for fluid administration, devices for biological use for manufacturing miniaturized microreactors, in electrophoresis processes, in DNA chip and other array applications, in integrated fuel cells, ink jet printers, and the like. Microchannels are used also, for example, for the refrigeration of devices located above microchannels.

One application of interest is the use of microchannels to make a miniaturized microreactor for diagnostic uses (see especially, U.S. Ser. No. 10/663,268 filed Sep. 16, 2003 and references cited therein, each which incorporated by reference in their entirety). A number of such devices are described for the amplification of nucleic acid, such as DNA or RNA, or for other biological tests, such as immunological detection of antigens in a biological sample. The microreactor can be combined with one or more integrated sample pretreatment chamber, micropump, heater, and also with integrated sample analysis features, such as an array of nucleic acid or antibody detectors. Such devices are described in more detail in U.S. Ser. No. 10/663,268, and related patents or applications.

However, complex procedures are traditionally required in order to form a microchannel system. In particular, conventional processes for forming embedded microchannels require so-called wafer bonding or opening structures from the backside of the wafer back.

A process for forming microchannels is described for example in the U.S. Pat. No. 6,376,291 granted on Apr. 23, 2002. In particular, this document describes a process for forming in a monocrystalline silicon body an etching-aid region for the monocrystalline silicon wherein a nucleus region is provided, surrounded by a protective structure and having a port extending along the whole etching-aid region.

According to the '291 patent, a polycrystalline layer is grown above the port in order to form a cavity completely embedded in the resulting wafer. Although advantageous from many aspects, the process described by the '291 patent is rather complex and it does not allow a completely crystalline final microstructure to be obtained.

The technical problem underlying the present invention is to provide a process for forming microchannels, having such structural and functional characteristics as to overcome the limits and drawbacks still affecting the processes according to the prior art.

SUMMARY OF THE INVENTION

The solution underlying the present invention is to use trench structures to obtain deep silicon cavities. A small surface port is used as a precursor for forming microchannels in an integrated structure. Through the port, a trench is defined and then etched to form the microchannel structure. The port is then closed by silicon to thus obtain a completely crystalline final structure.

BRIEF DESCRIPTION OF THE DRAWINGS

A more complete understanding of the method and apparatus of the present invention may be acquired by reference to the following Detailed Description when taken in conjunction with the accompanying Drawings wherein.

DETAILED DESCRIPTION OF THE DRAWINGS

The invention relates particularly, but not exclusively, to a process for realizing miniaturized microchannels buried in a completely monocrystalline array and the following description is made with reference to this field of application for convenience of illustration only.

Figure 1:
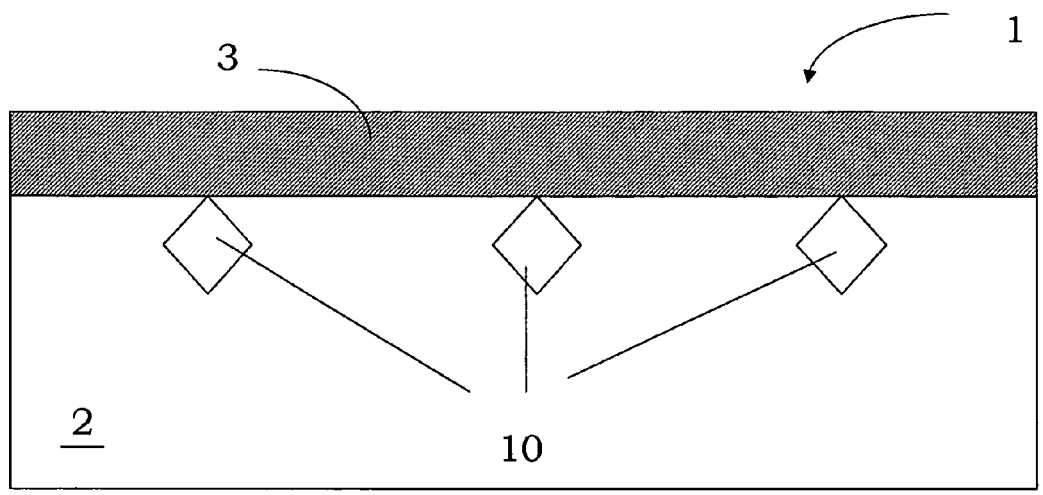
FIG. 1 schematically shows a section of an integrated structure with at least a microchannel realized with the process according to the invention.

With reference to the drawings, and particularly to FIG. 1, an integrated structure comprising a plurality of microchannels 10 formed according to the invention is globally and schematically indicated with reference 1.

In particular, the integrated structure 1 comprises a monocrystalline silicon substrate 2 whereon a monocrystalline silicon layer 3 is grown.

The monocrystalline silicon layer 3 is obtained in turn by epitaxial growth on convenient cavities (rhombohedral in the example shown) of said microchannels 10 without using coverings.

Advantageously, according to the invention, microchannels 10 are completely buried in the substrate 2 and the final integrated structure 1 is completely monocrystalline.

The steps of the process according to the invention for forming buried microchannels 10 in a completely monocrystalline integrated structure 1 are now described. As it will be seen in the following description, advantageously, according to the invention, these miniaturized channels are completely obtained through surface micromachining processes.

The process for forming buried microchannels 10 in an integrated structure 1 according to the invention comprises the steps of:

providing a monocrystalline silicon substrate 2;

forming on the substrate 2 surface a silicon nitride mask (Hard mask) through a CVD deposition technique; and opening of a window having a convenient width L through photolithographic systems and following plasma etching.

Figure 2:
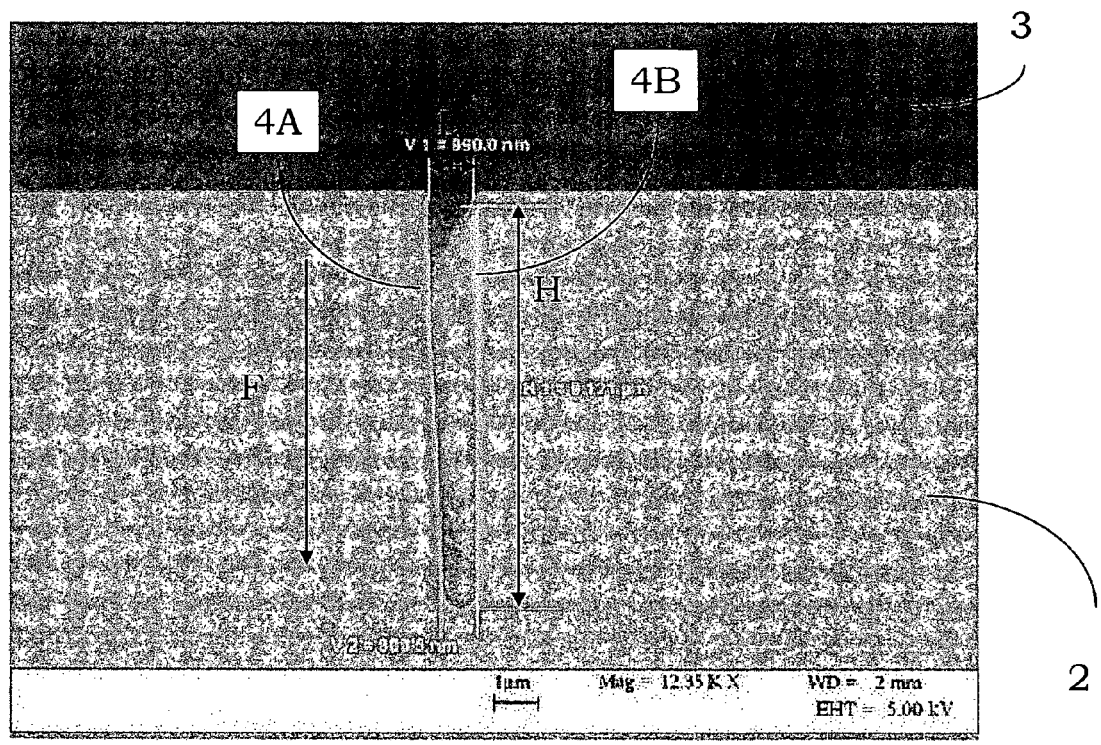
FIGS. 2, 3A, 3B and 4 are micrographs of the integrated structure of FIG. 1 in different steps of the process according to the invention.

In particular, as it is schematically shown in FIG. 2, above the substrate 2 a window is opened having a width L of about 1 mm and a depth H of about 9 mm along the substrate 2 direction, indicated in figure with the arrow F.

Advantageously according to the invention, the process provides a following plasma etching which uses the hard mask to form deep trenches 4 in the substrate 2, as shown in FIG. 2. Trenches 4 have side walls 4A and 4B which are substantially orthogonal to the substrate 2 surface.

The resulting structure then undergoes a further anisotropic wet etching, for example with a TMAH or KOH solution.

It is worth noting that solutions with different KOH or TMAH concentrations etch the monocrystalline silicon of the substrate 2 with speeds which highly depend on the crystallographic orientations and the dopant concentration of the substrate 2 itself. It is thus possible, by using a TMAH- or KOH-solution-etching, to form highly controllable and reproducible three-dimensional microchannels 10.

Advantageously according to the invention, trenches 4 are the precursors of microchannels 10.

Figure 3A:
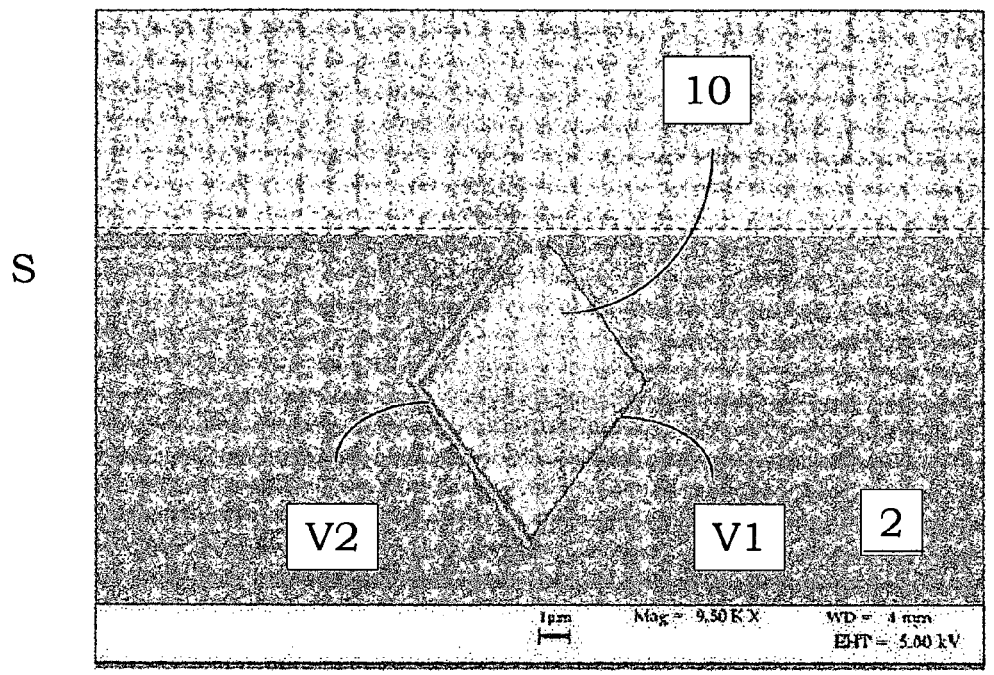
Figure 3B:
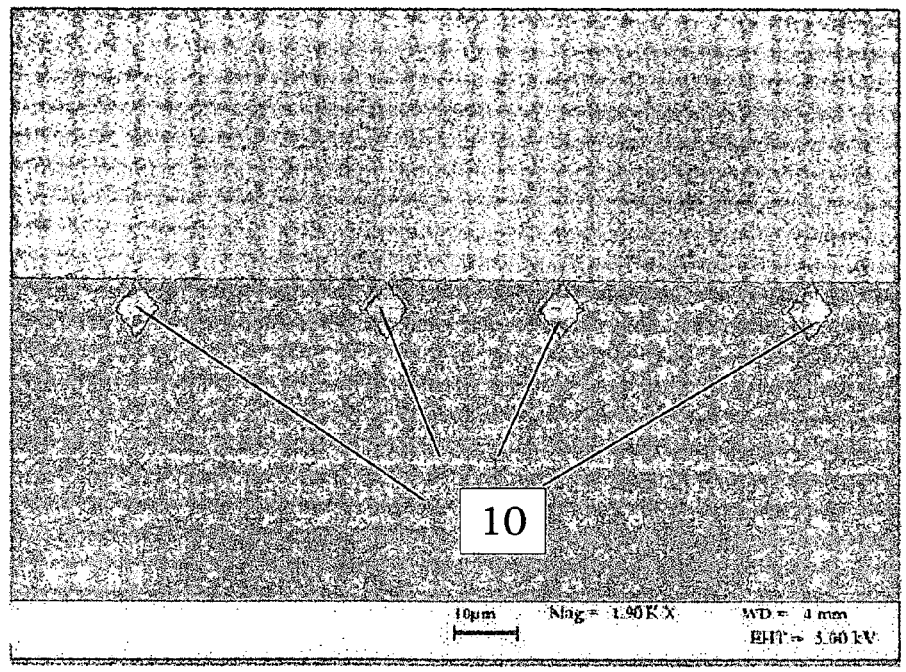

The integrated structure 1, after the anisotropic etching step, has the shape shown in FIGS. 3A and 3B, wherein a single microchannel or a plurality of microchannels are shown, respectively.

Advantageously according to the invention, the resulting microchannels 10 have a rhombohedral shape.

In particular, the original shape of trenches 4 (shown in FIG. 2) turns into a pair of so-called rotated v-grooves V1 and V2, orthogonal to the surface S of the substrate 2 and defining rombohedron-shaped microchannels 10, as shown in FIG. 3A.

In other words, a bottleneck-shaped deep cavity is obtained, which has a small port on the surface S of the substrate 2.

Figure 4:
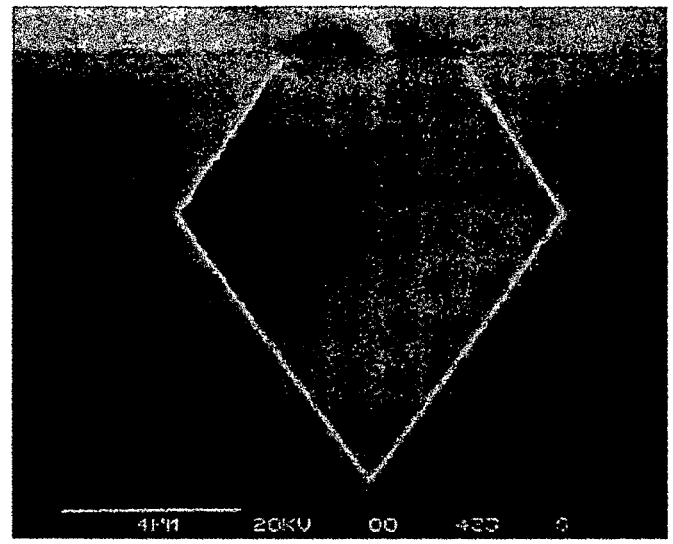

In practice, while the etching time passes, because of the presence of a so-called under cut under the hard mask on the substrate 2 surface, microchannels 10 open upwardly changing the symmetry between the upper and lower part of their cavity, as schematically shown in FIG. 4.

Figure 5:
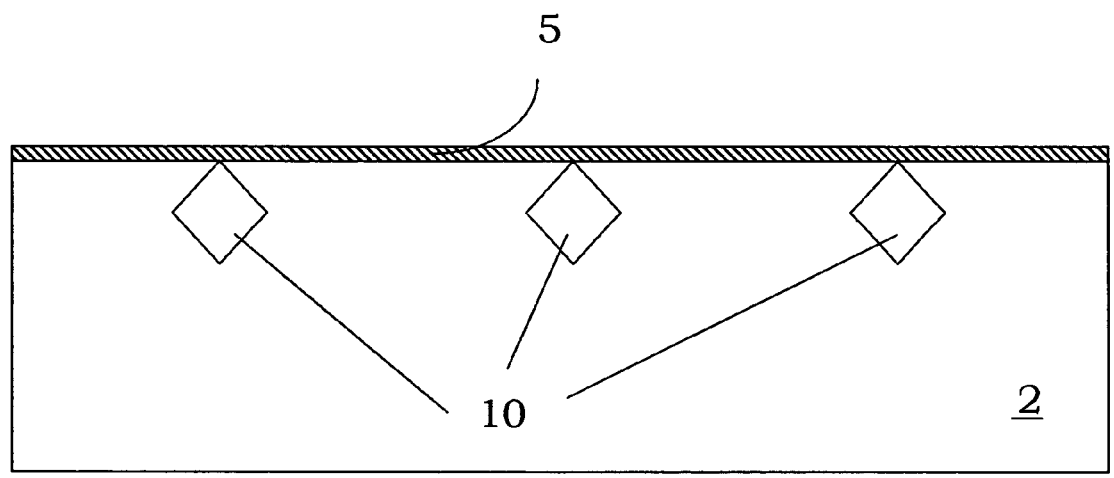
FIG. 5 schematically shows an integrated structure with microchannels realized according to an alternative embodiment of the process according to the invention.

It is, however, possible, by limiting the etching time, to obtain conveniently-sized microchannels by enlarging the depth of original trenches 4. In the alternative, it is possible to exploit the so-called etch stop effect by using as hard mask a heavily doped monocrystalline layer, as schematically shown in FIG. 5, wherein the substrate 2 and microchannels 10 are covered by a heavily doped hard mask layer capable of reducing under cut effects even when the substrate 2 etching time passes.

In a preferred embodiment, the layer 5 has a dopant concentration (for example, boron) higher than $10^{19}$ atoms/$cm^3$.

It is also possible to use a predeposition on trench 4 walls of a layer of material 6 having a low etching speed (as, for example, the nitride).

In particular, this alternative embodiment of the process according to the invention provides a deposition of a nitride layer 6 followed by a plasma etching effective to open a region 7 at the trench 4 base, as shown in FIGS. 6A to 6F.

Figure 6A:
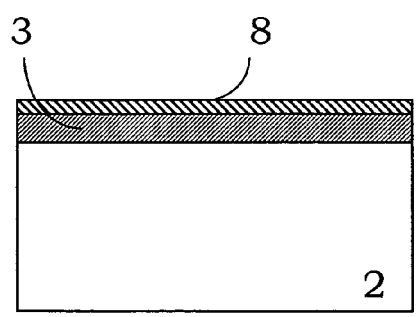
FIGS. 6A–6F schematically show an integrated structure with microchannels in different steps of a further alternative embodiment of the process according to the invention.
Figure 6B:
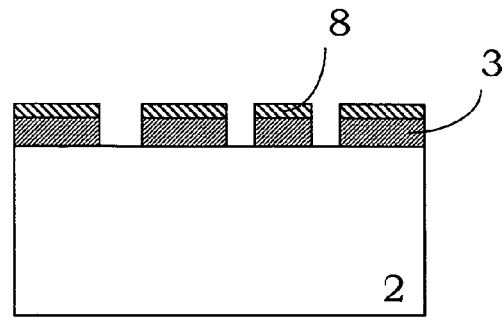

The process for realizing buried microchannels 10 in an integrated structure 1 according to this alternative embodiment of the invention comprises the steps of:

providing a monocrystalline silicon substrate 2;

growing a monocrystalline silicon layer 3 above the substrate 2; and forming a mask by means of a photoelectric film 8 above the monocrystalline silicon layer 3, as schematically shown in FIG. 6A.

Figure 6C:
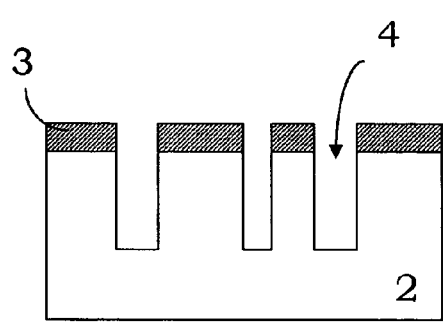
Figure 6D:
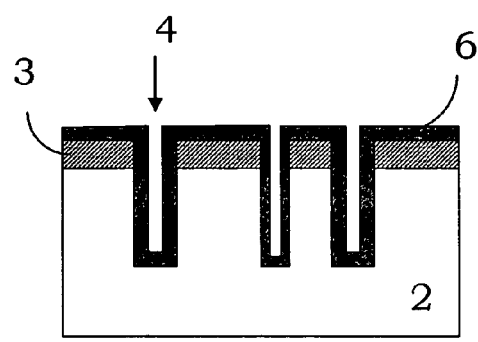
Figure 6E:
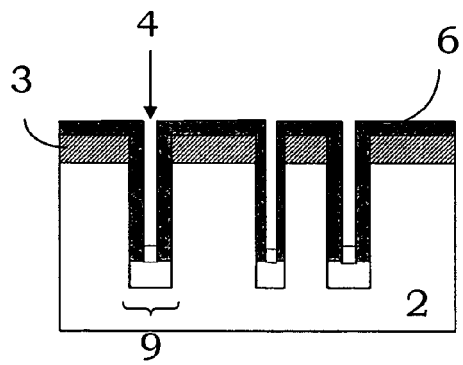

The process provides thus the steps of:

opening a plurality of windows through photolithographic systems and following plasma etching (FIG. 6B); and forming a plurality of trenches 4 in correspondence with the plurality of windows (FIG. 6C).

Figure 6F:
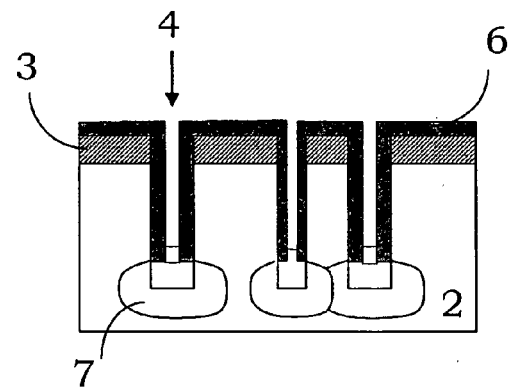

Advantageously this alternative embodiment of the process according to the invention, provides therefore a deposition step of a nitride layer 6 (FIG. 6D), a removing step of the layer 6, an etching step of the silicon substrate in a lower part 9 of trenches 4 (FIG. 6E) and a plasma etching step effective to open a plurality of regions 7 at the trench 4 base (FIG. 6F).

In particular, the plasma etching step to open regions 7 at the trench 4 base is activated only in the area wherein the nitride layer 6 has been removed. It is essentially a so-called SCREAM process, wherein trench 4 walls are protected to localize the etching only under the trench base.

Even using this alternative embodiment of the process according to the invention, deep regions 7 are thus obtained, which have however a small surface opening in correspondence with the opening areas of trenches 4.

Advantageously according to the invention, trenches 4 are used for an anisotropic etching effective to obtain rhombohedral microchannels. The shape obtained is due to the different etching speeds of the different crystallographic directions.

The side walls 4A and 4B of trenches 4 undergo the etching anisotropic action and the erosion continues with different etching speeds due to the different atom coordination (in terms of bond quantity of silicon atoms directed towards the substrate).

In particular, atoms on planes of the (100) type have coordination two (i.e., two bonds directed towards the substrate), whereas atoms on planes of the (111) type have coordination three (i.e., three bonds directed towards the bulk); that is that they are more bonded.

Trenches 4 are directed along the directions (110) on the wafer surface of the (100) type. Planes (111) find on the wafer surface just the direction (110) and they are rotated with respect to the normal to the surface by about 54.7°.

In particular two planes are present, which pass in the upper part of trenches 4 and two planes passing in the lower part. All atoms along these directions have coordination three.

Advantageously according to the invention, the process starts by eroding the atoms having the lowest coordination which are characterized by a higher speed. After reaching the directions of planes (111) passing through/from the upper part and through/from the lower part of trenches 4, speed decreases by about a hundred times since it finds only atoms with coordination three, therefore it continues with the etching speed of planes (111) as shown in FIGS. 3A and 3B. In particular, a microchannel 10 opened towards the substrate 2 surface is obtained.

Advantageously, according to the invention, deep silicon cavities are thus obtained, being characterized by a small surface port whereto it is possible to apply a silicon deposition step to obtain a monocrystalline structure.

In other words, microchannels 10 have a bottle-section-shaped or rhomohedral precursor (obtained as above described) which is easily closed epitaxially in one embodiment or closed by deposition of a layer such as an oxide, polysilicon, nitride or other convenient material.

Figure 7A:
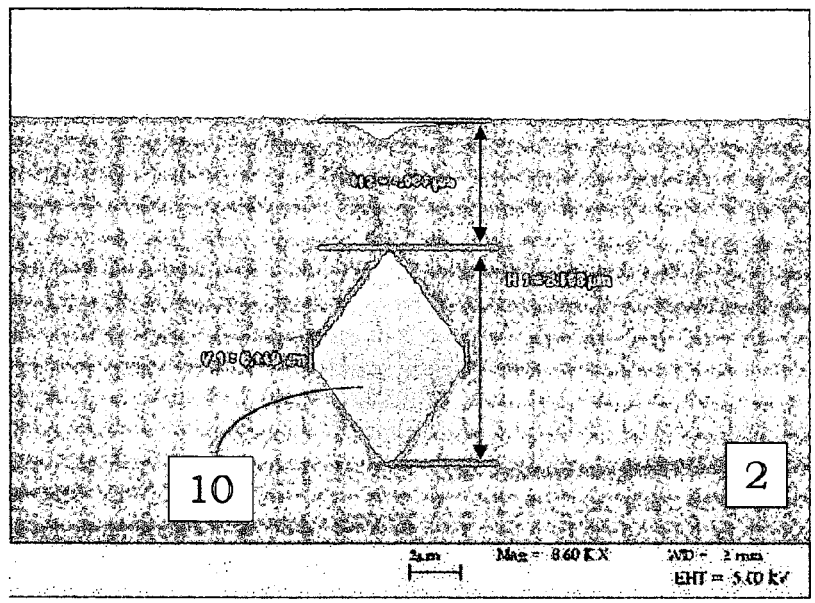
FIGS. 7A and 7B show micrographs of the final integrated structure with microchannels realized with the process according to the invention.

Advantageously according to the invention, the process provides a further epitaxial new growth step corresponding to the material used to close the upper part of the microchannel 10, as shown in FIG. 7A. It is thus possible to obtain completely buried monocrystalline silicon microchannels 10.

Figure 7B:
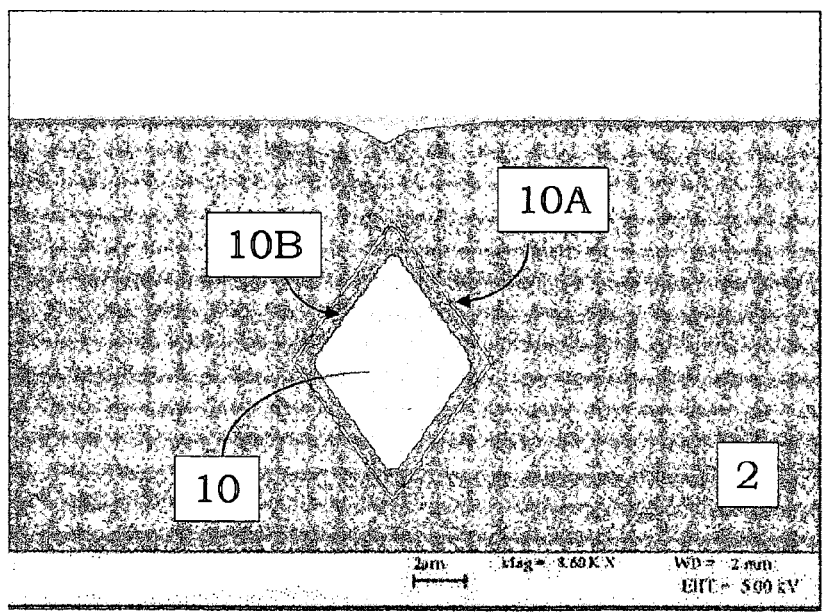

FIG. 7B shows for completeness the channel profile before (10A) and after (10B) the epitaxial new growth step. It happens thus that the monocrystalline material deposition occurs consistently also inside the microchannel 10.

It is also possible to close the upper part of microchannels by using other deposition techniques such as oxide or polysilicon or nitride deposition.

In conclusion, the process for realizing microchannels 10 buried in an integrated structure 1 according to the invention allows, thanks to the resulting etching form, the structure of the microchannel under the substrate 2 surface to be enlarged, but to keep, at the same time, the etching port small by means of trenches 4. The surface microchannel closing is thus performed by growing epitaxially the material.

Advantageously, according an embodiment of the invention, the integrated structure 1 is completely epitaxial even above microchannels 10 and it is performed by exploiting a deep cavity characterized by a small surface opening, which can be obtained in several kinds of processes, as well as an easy epitaxial new growth of this cavity.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A process for realizing fluid microchannels buried in an integrated structure comprising a monocrystalline silicon substrate, comprising:
   forming in said substrate at least a trench; and
   obtaining said fluid microchannels starting from a deep cavity characterized by a small surface port obtained through anisotropic etching of said at least one trench, said fluid microchannels being nearly entirely buried in said substrate in a completely monocrystalline structure which closes the surface port along a certain length of the fluid microchannel.

2. The process according to claim 1:
   wherein forming comprises:
      depositing a mask above said substrate;
      opening of windows having a convenient width; and
      plasma etching which uses said mask to form said trenches having side walls being essentially orthogonal to the surface of said substrate; and
   wherein obtaining comprises:
      wet anisotropic etching to form, starting from said trenches, said fluid microchannels, said anisotropic etching step providing different etching speeds due to different atom coordination.

3. The process according to claim 2, wherein anisotropic etching is performed with a TMAH or KOH solution.

4. The process according to claim 2, wherein opening the windows having a convenient width is performed through photolitographraphy and subsequent plasma etching.

5. The process according to claim 2, wherein deposition of a mask above said substrate comprises a silicon nitride deposition through the CVD deposition.

6. The process according to claim 2, wherein deposition of a mask above said substrate comprises a heavily doped monocrystalline layer deposition.

7. The process according to claim 6, wherein the heavily doped monocrystalline layer has a dopant concentration higher than $10^{19}$ atoms/cm$^3$.

8. The process according to claim 1, further comprising a convenient epitaxial new growing operation effective to close an upper part of said fluid microchannels and completely bury the fluid microchannels in monocrystalline silicon.

9. The process according to claim 1, further comprising an oxide, polysilicon or nitride deposition effective to close an upper part of said fluid microchannels and completely bury the fluid microchannels.

10. The process according to claim 1, wherein the wet anisotropic etching step turns said side walls of said trenches into a pair of rotated v-grooves orthogonal to a surface of said substrate and defining rombohedron-shaped fluid microchannels.

11. The process according to claim 1, further comprising depositing a layer of material having a low etching speed.

12. The process according to claim 11, further comprising plasma etching effective to open a region at a trench base.

13. The process according to claim 11, further comprising removing of said layer and in an etching of said substrate in a lower part of said trenches before said plasma etching step.

14. A method for forming fluid microchannels, comprising:
   forming a narrow elongated trench in a monocrystalline silicon substrate;
   performing an anisotropic wet etch of the narrow elongated trench to form a fluid microchannel structure having a generally rhombohedral cross-sectional shape with a top port substrate surface opening; and
   closing the top port substrate surface opening of the fluid microchannel structure along a certain length of elongated trench to entirely enclose the fluid microchannel structure.

15. The method of claim 14 wherein closing comprises epitaxially growing monocrystalline silicon on a surface of the substrate to entirely enclose the fluid microchannel structure in monocrystalline silicon.

16. The method of claim 14 wherein the anisotropic wet etch is made using a TMAH solution.

17. The method of claim 14 wherein the anisotropic wet etch is made using a KOH solution.

18. The method of claim 14 wherein forming comprises defining a mask with an opening therein at the location of the trench and plasma etching though the mask opening to form the narrow elongated trench.

19. The method of claim 14 wherein the narrow elongated trench has a width at the surface of the substrate of about 1 micrometer.

20. The method of claim 19 wherein the narrow elongated trench has a depth from the surface of the substrate of about 9 micrometers.

21. The method of claim 14 wherein closing comprises depositing a layer of material to close the top port substrate surface opening.

22. The method of claim 21 wherein layer of material is a material taken from the group consisting of a polysilicon, a nitride or an oxide.

23. A method for forming fluid microchannels, comprising:
   forming a monocrystalline silicon layer over a monocrytalline silicon substrate;
   forming a narrow elongated trench through the monocrystalline layer and into the monocrystalline silicon substrate;
   performing an etching of a base region of the narrow elongated trench to form a fluid microchannel structure having a top port opening; and
   closing the top port opening of the fluid microchannel structure along a certain length of the elongated trench to entirely enclose the fluid microchannel structure.

24. The method of claim 23 wherein closing comprises growing monocrystalline silicon to close the top port opening in trench above the formed fluid microchannel structure and produce the fluid microchannel structure enclosed completely in monocrystalline silicon.

25. The method of claim 23 wherein performing comprises anisotropically wet etching the base region to define the fluid microchannel structure with a generally rhombohedral cross-sectional shape.

26. The method of claim 25 wherein the anisotropic wet etch is made using a TMAH solution.

27. The method of claim 25 wherein the anisotropic wet etch is made using a KOH solution.

28. The method of claim 23 wherein forming the narrow elongated trench comprises defining a mask with an opening therein at the location of the trench and plasma etching though the mask opening to form the narrow elongated trench.

29. The method of claim 23 wherein closing comprises depositing a layer of material to close the top port opening.

30. The method of claim 29 wherein layer of material is a material taken from the group consisting of a polysilicon, a nitride or an oxide.

31. A process, comprising:
   forming an elongated trench in a monocrystalline silicon substrate;
   anisotropic etching of said elongated trench to obtain a deep cavity characterized by an elongated surface port; and
   closing at least a portion of the elongated surface port of the elongated trench to define with the deep cavity in the silicon substrate a tunnel-like microchannel.

32. The process of claim 31 wherein forming the elongated trench comprises plasma etching the substrate through a mask to form said trench having side walls being essentially orthogonal to the surface of said substrate.

33. The process of claim 32 wherein anisotropic etching comprises wet anisotropic etching to form, starting from said trench, said deep cavity, said anisotropic etching providing different etching speeds due to different atom coordination.

34. The process of claim 31, wherein closing comprises epitaxial new growing so as to close the elongated surface port and bury the deep cavity in monocrystalline silicon.

35. The process of claim 31, wherein closing comprises an oxide, polysilicon or nitride depositing effective to close close the elongated surface port and bury the deep cavity.

* * * * *

UNITED STATES PATENT AND TRADEMARK OFFICE
CERTIFICATE OF CORRECTION

| | | |
|---|---|---|
| PATENT NO. | : 7,063,798 B2 | Page 1 of 1 |
| APPLICATION NO. | : 10/726264 | |
| DATED | : June 20, 2006 | |
| INVENTOR(S) | : Alessio Maria D'arrigo Giuseppe et al. | |

It is certified that error appears in the above-identified patent and that said Letters Patent is hereby corrected as shown below:

Title page, item Replace "Alessio M. D'arrigo Guiseppe"
(75) Inventors: Line 1 With --Alessio M. D'arrigo Giuseppe--

Title page, Replace "Guiseppe Arena"
(75) Inventors: Lines 3-4 With --Giuseppe Arena--

Signed and Sealed this

Twenty-seventh Day of March, 2007

JON W. DUDAS
*Director of the United States Patent and Trademark Office*